United States Patent [19]

Kankkunen

[11] Patent Number: 5,799,710
[45] Date of Patent: Sep. 1, 1998

[54] ARRANGEMENT IN CONNECTION WITH AN ANAESTHETIC LIQUID CONTAINER

[75] Inventor: Jukka Kankkunen, Vantaa, Finland

[73] Assignee: Instrumentarium Oy, Helsinki, Finland

[21] Appl. No.: 774,211

[22] Filed: Dec. 27, 1996

[30] Foreign Application Priority Data

| Dec. 29, 1995 | [FI] | Finland | 956354 |
| Apr. 18, 1996 | [FI] | Finland | 961698 |
| Dec. 11, 1996 | [FI] | Finland | 964867 |

[51] Int. Cl.$^6$ ............................................. B65B 1/04
[52] U.S. Cl. ............................ 141/18; 141/59; 141/198; 141/285
[58] Field of Search .................. 141/2, 18, 21, 141/45, 59, 61, 198, 285, 286, 289–295, 308, 309, 346–352, 363–366, 311 A, 319–321, 353–355, 357, 382, 115–120; 128/200.19, 200.16, 200.21; 261/DIG. 65; 137/207.5

[56] References Cited

U.S. PATENT DOCUMENTS

| 3,536,108 | 10/1970 | Schreiber | 141/18 |
| 3,565,133 | 2/1971 | Jones . | |

FOREIGN PATENT DOCUMENTS

| 4106756 | 9/1992 | Germany . |
| 2279016 | 12/1994 | United Kingdom . |

Primary Examiner—Henry J. Recla
Assistant Examiner—Steven O. Douglas
Attorney, Agent, or Firm—Andrus, Sceales, Starke & Sawall

[57] ABSTRACT

An arrangement in connection with an anaesthetic, liquid container, said arrangement comprising a device for conducting anaesthetic liquid during emptying of the anaesthetic liquid container from the anaesthetic liquid container to a transport or supply container connected to a filling port of the anaesthetic liquid container, and vice versa during the filling of the anaesthetic liquid container, and a device for removing a volume of gas equivalent to the volume of anaesthetic liquid during emptying of the anaesthetic liquid container from the transport or supply container and during filling correspondingly from the anaesthetic liquid container. To allow the anaesthetic liquid container to be emptied effectively, an intermediate container which is provided in connection with the anaesthetic liquid container and formed from a curved tubular portion and which during the filling of the anaesthetic liquid container forms a common conduit for the anaesthetic liquid and the gas removed from the liquid container is adapted during the emptying of the anaesthetic liquid container to form a conduit at least for the anaesthetic liquid discharged from the anaesthetic liquid container.

24 Claims, 5 Drawing Sheets

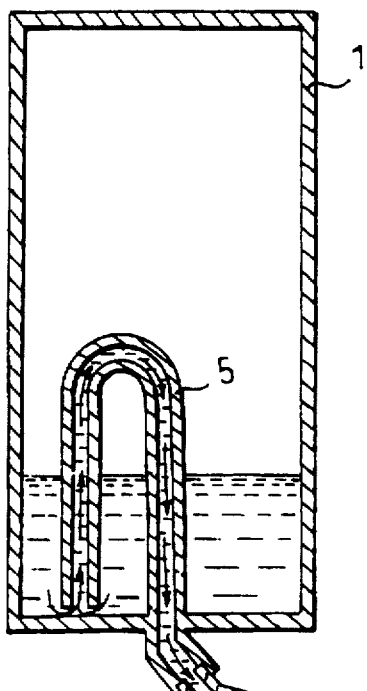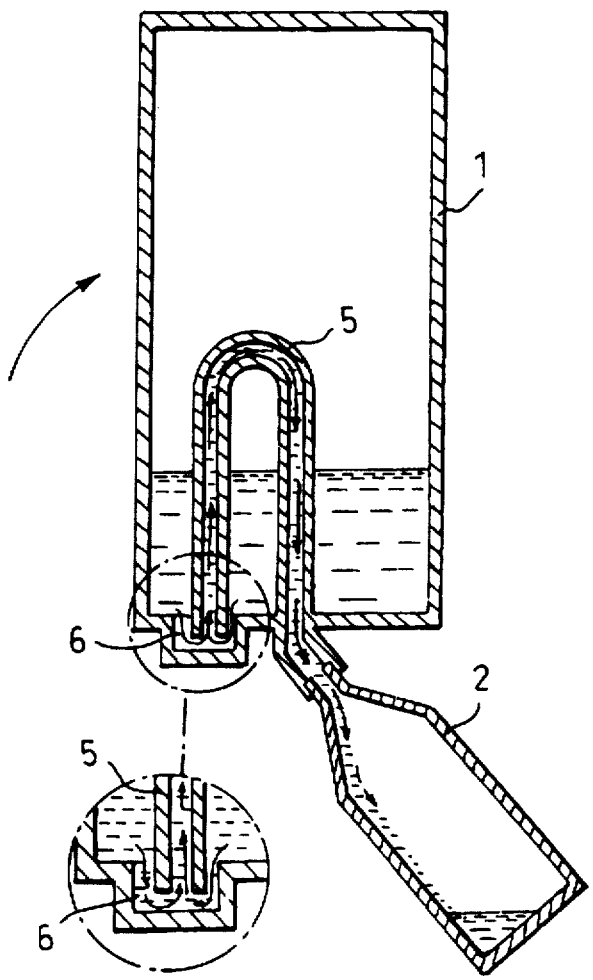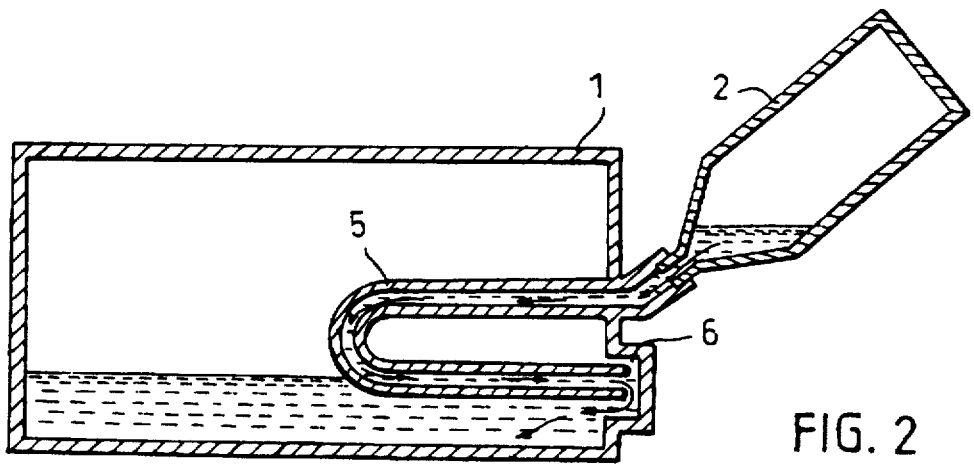

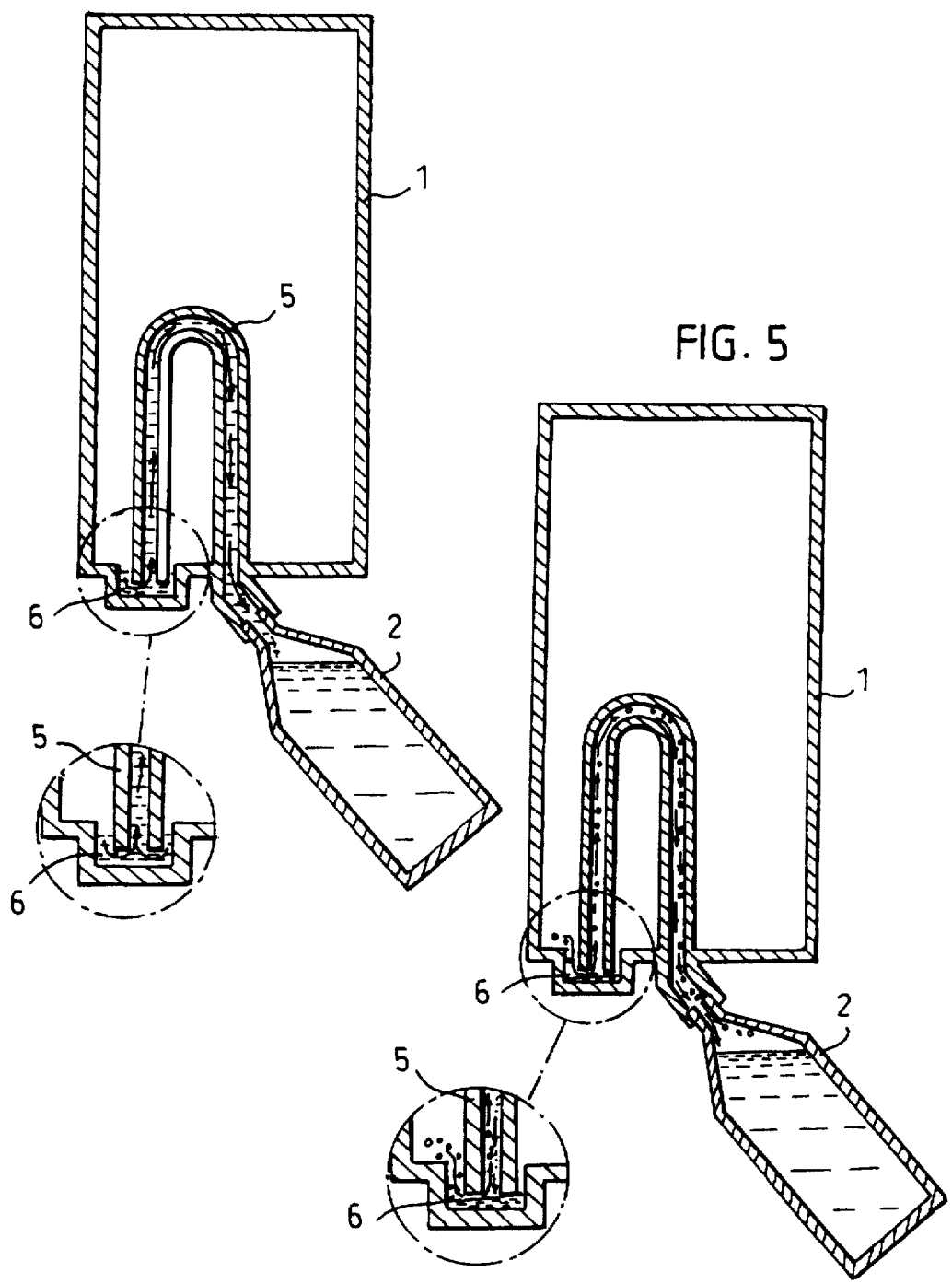

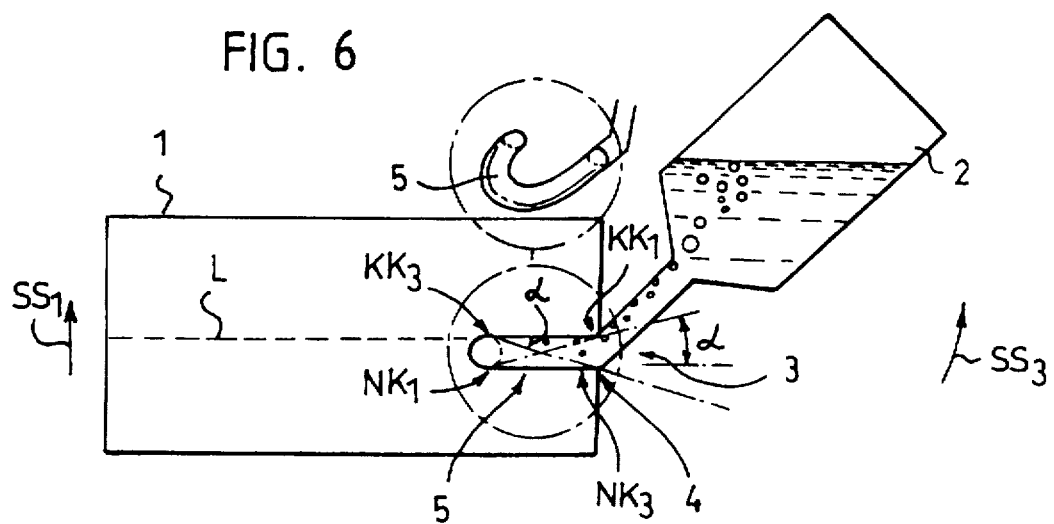
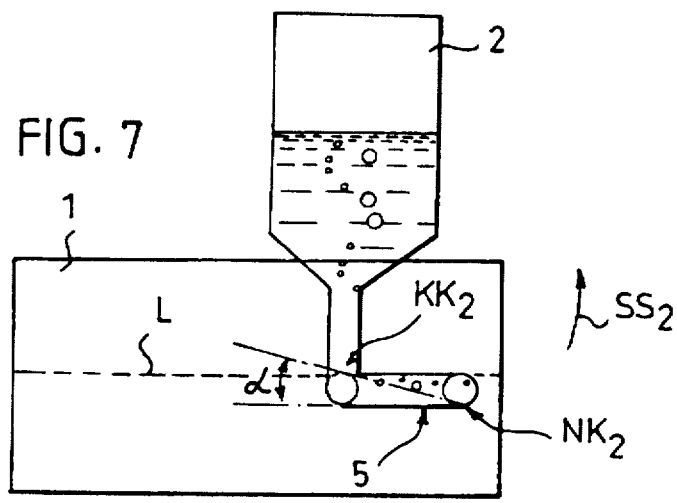
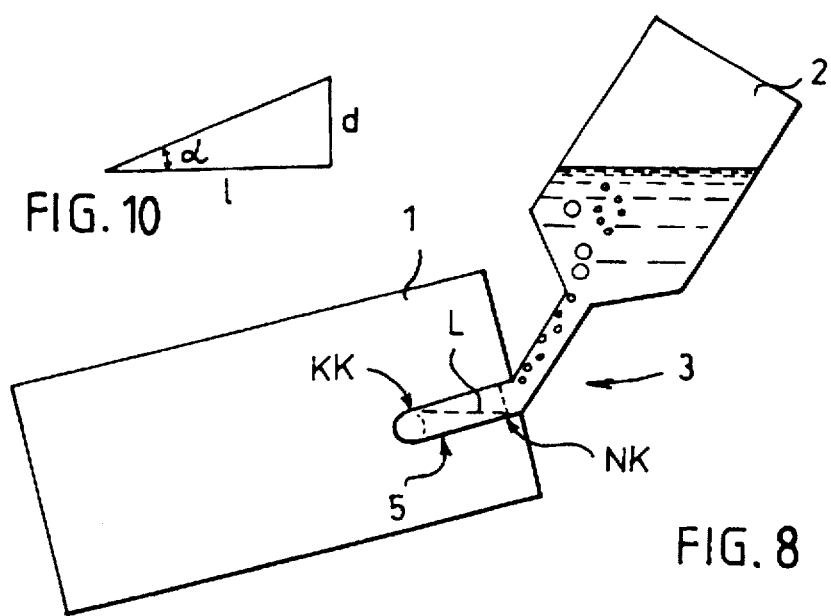

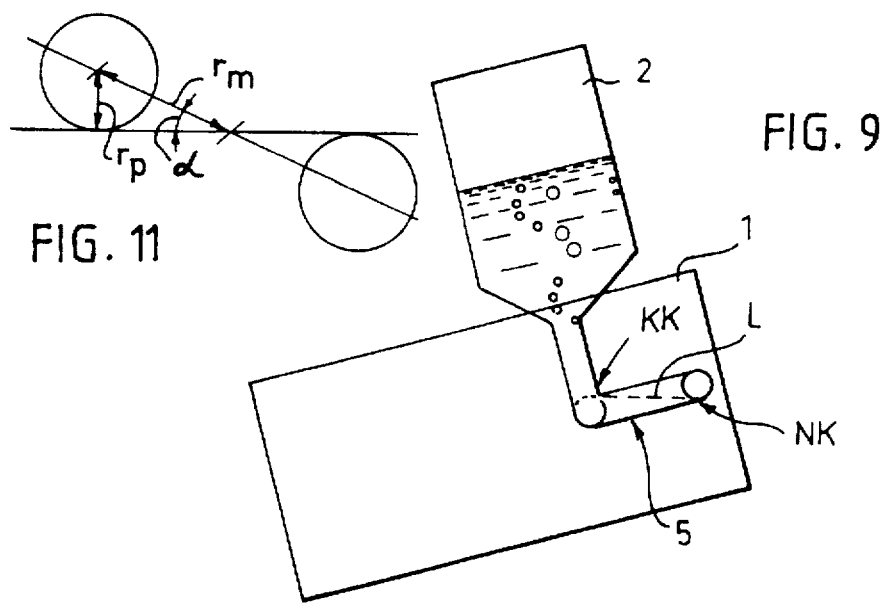
FIG. 9
FIG. 11
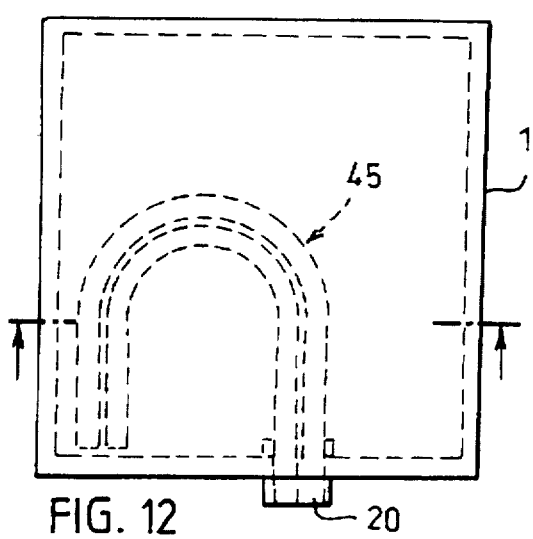
FIG. 12
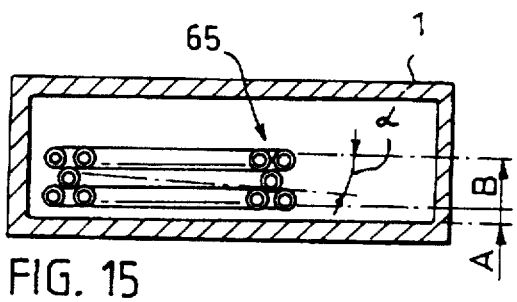
FIG. 15
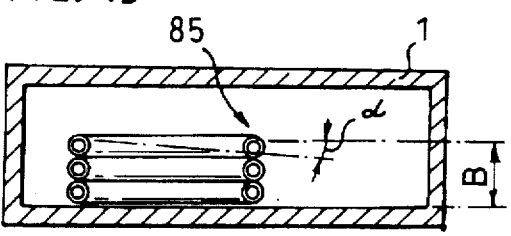
FIG. 17
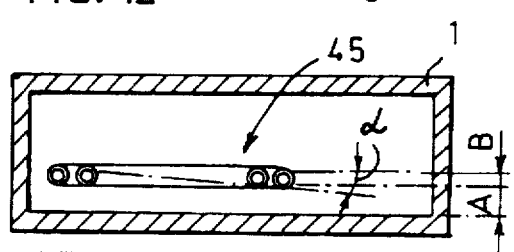
FIG. 13
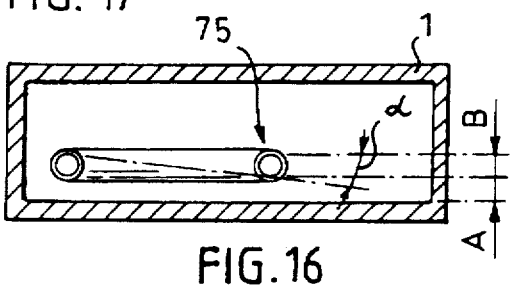
FIG. 16
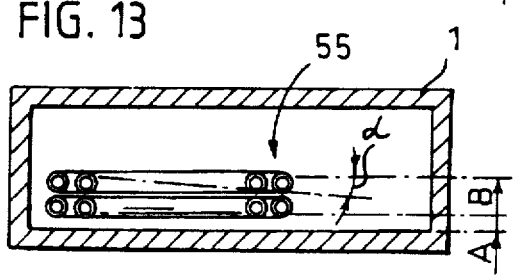
FIG. 14

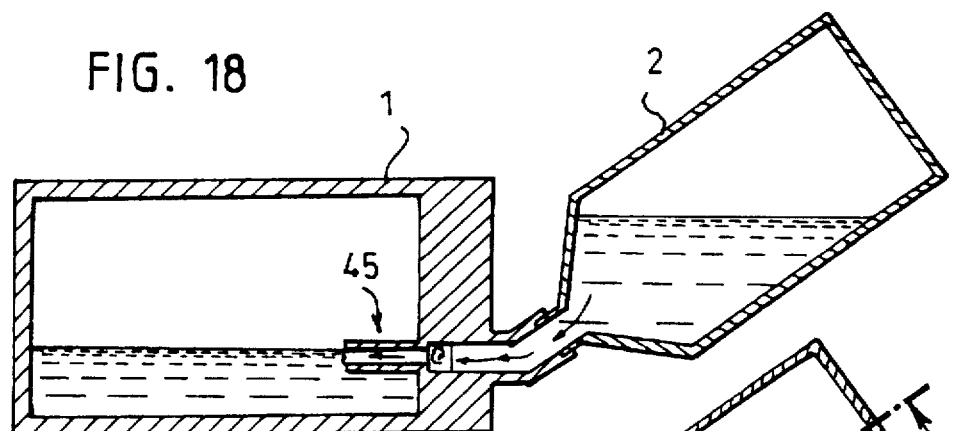
FIG. 18
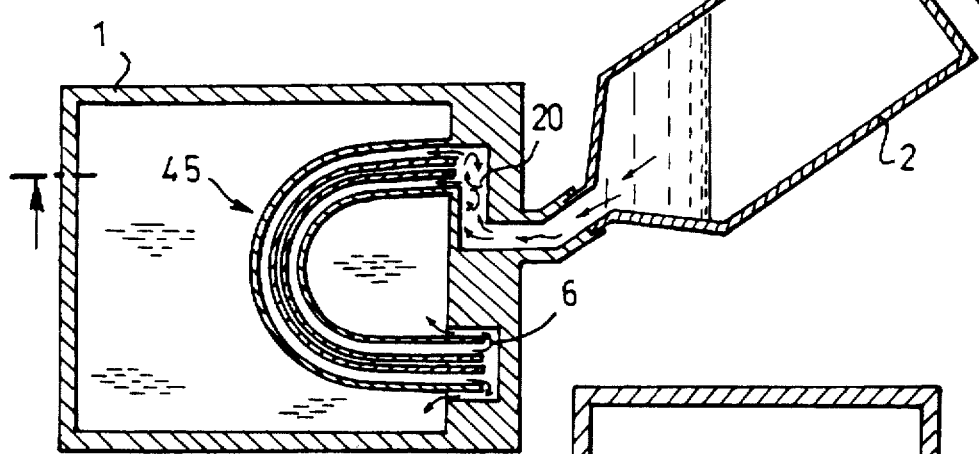
FIG. 19
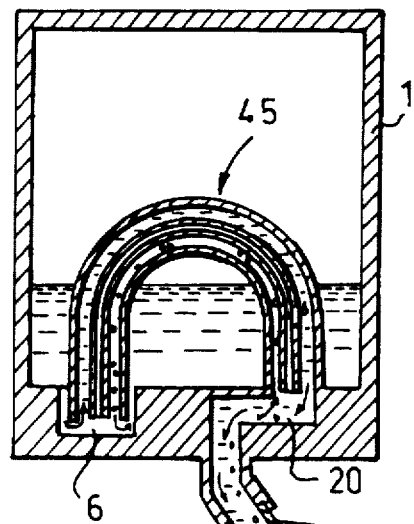
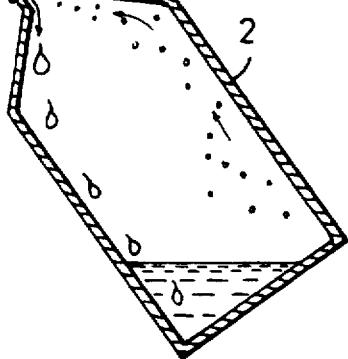
FIG. 20

ARRANGEMENT IN CONNECTION WITH AN ANAESTHETIC LIQUID CONTAINER

The invention relates to an arrangement in connection with an anaesthetic liquid container, said arrangement comprising means for conducting anaesthetic liquid during emptying of the anaesthetic liquid container from the anaesthetic liquid container to a transport or supply container connected to a filling port of the anaesthetic liquid container, and vice versa during the filling of the anaesthetic liquid container, and means for removing a volume of gas equivalent to the volume of anaesthetic liquid during emptying of the anaesthetic liquid container from the transport or supply container and during filling correspondingly from the anaesthetic liquid container.

An anaesthetic liquid container is emptied in practice for instance by turning the liquid container so that the liquid surface is above the transport or supply container, whereby the anaesthetic liquid flows from the liquid container to the transport or supply container. In principle, the anaesthetic liquid container can be emptied through the same conduit system that is used for filling it. However, it has been found in practice that it is rather complicated to perform the emptying in such a way that the container becomes totally empty. For the above reasons, there are prior art solutions in which the container is emptied through a separate discharge conduit and valve members mounted in connection with it. An example of such a solution is the apparatus disclosed in U.S. Pat. No. 3,565,133.

The use of a separate discharge conduit often results in a complicated solution which has the drawback of high manufacturing costs. A complex structure also increases the operating costs, the number of spare parts needed, etc.

It is an object of the invention to provide an arrangement by which the drawbacks of the prior art can be eliminated. This is achieved with an arrangement of the invention, which is characterized in that an intermediate container which is provided in connection with the anaesthetic liquid container and formed from a curved tubular portion and which during the filling of the anaesthetic liquid container forms a common conduit for the anaesthetic liquid and the gas removed from the liquid container is adapted during the emptying of the anaesthetic liquid container to form a conduit at least for the anaesthetic liquid discharged from the anaesthetic liquid container.

The most significant advantage of the invention is that it allows an anaesthetic liquid container to be emptied extremely advantageously as effectively as possible. A further advantage of the invention is that the container can be emptied advantageously by the same means that are used for filling it; no separate discharge conduit with associated valves and other similar components are required.

In the following, the invention will be described in greater detail by means of the preferred embodiments illustrated in the accompanying drawings, in which FIG. 1 is a schematic view of the basic principle of the arrangement according to the invention, FIGS. 2 to 5 show an embodiment of the arrangement of the invention during different emptying steps, FIGS. 6 to 9 illustrate the operation of an essential part of the arrangement according to the invention in different situations during filling, FIGS. 10 and 11 are schematic views of certain aspects of FIGS. 6 to 9, FIGS. 12 to 17 show different embodiments of the arrangement of the invention, and FIGS. 18 to 20 illustrate schematically the operation of the embodiment of FIGS. 12 and 13 in different situations.

FIG. 1 is a schematic view of the basic principle of the arrangement of the invention. Reference numeral 1 indicates an anaesthetic liquid container, and reference numeral 2 designates an anaesthetic liquid transport or supply container, such as a bottle.

FIG. 1 shows a situation where the combination of the anaesthetic liquid container 1 and the transport or supply container 2 connected to it have been turned to a position in which the anaesthetic liquid drains out of the container.

According to the basic idea of the invention, the container 1 is emptied by the use of a component mounted in the container 1 for filling, i.e. an intermediate container 5 formed by a curved tubular portion. The intermediate container is arranged during the filling of the anaesthetic liquid container 1 to form a common conduit for the anaesthetic liquid and the gas removed from the container 1. The intermediate container formed by a curved tubular portion is used during the emptying of the container to carry the anaesthetic liquid draining out of the container to a transport or supply container , as shown in FIG. 1. The emptying is based on siphonage, as will be explained more closely in the following with reference to FIGS. 2 to 5.

FIGS. 2 to 5 illustrate the arrangement of the invention in different steps of emptying the container 1. As stated above, the intermediate formed by a curved tubular portion is mounted in the anaesthetic liquid container 1 in such a way that it can suck the anaesthetic liquid out by siphonage pressure so that the container is emptied. The intermediate container 5 is thus positioned between a filling port 4 and the inner space of the anaesthetic container 1 in such a way that the free end of the intermediate container 5 is as close as possible to that wall of the anaesthetic liquid container 1 which is the lowest when the container 1 is in the emptying position, i.e. in the position of e.g. FIGS. 1 and 3. It has been found that the best emptying result is obtained when the free end of the tubular portion forming the intermediate container 5 is positioned in a liquid collection sump 6, where the anaesthetic liquid collects in the emptying position of the anaesthetic liquid container 1. The dimensions of the liquid collection sump 6 and the intermediate container 5 determine the amount of liquid that will remain in the anaesthetic liquid container 1. FIGS. 2 to 5 show such an embodiment, which is particularly suitable for use when the anaesthetic liquid is desfluran.

The emptying of the anaesthetic liquid container is started according to FIG. 2 by allowing a small amount of an anaesthetic to flow from a transport or supply container 2 to the anaesthetic liquid container 1; this equalizes the pressures in the anaesthetic liquid container 1 and in the transport or supply container 2, and the intermediate container 5 formed by the tubular portion is filled with the anaesthetic. During the above-mentioned step, the anaesthetic liquid container 1 is turned to a position according to FIG. 3. The turning of the anaesthetic liquid container 1 is indicated in FIG. 3 by an arrow. When the anaesthetic liquid container 1 is in the position according to FIG. 3, the liquid flow direction is reversed, and the anaesthetic flows from the liquid container to the transport or supply container 2. FIG. 4 illustrates a situation where the anaesthetic liquid container is almost empty, and the anaesthetic has collected in the liquid collection sump 6. The emptying of the anaesthetic liquid container 1 stops when the tubular portion forming the intermediate container receives replacement gas as shown in FIG. 5, or when the container is turned to the normal operative position.

One of the advantages of the invention is that the intermediate container 5 can be formed from the intermediate container used for overfill prevention during filling. The formation of the intermediate container in such a case will be described in the following. FIGS. 6 to 9 illustrate the principle according to which the intermediate container is formed. In FIGS. 6 to 9, the same reference numerals have the same significance as in FIGS. 1 to 5. An anaesthetic liquid is supplied to an anaesthetic liquid container 1 from a transport or supply container 2, such as a bottle. The construction further comprises means 3 for conducting the anaesthetic liquid into the anaesthetic liquid container 1 for vaporization and for removing an amount of gas equivalent to the filling of anaesthetic liquid from the anaesthetic liquid container 1 and for conducting the replacement gas into the supply container 2. The means 3 comprise, for example, a conduit through which the anaesthetic liquid and the volume of gas equivalent to the volume of liquid can flow into and out of the container, and necessary connector means for fixing the supply container 2 tightly to the filling port 4 of the anaesthetic liquid container.

The above-mentioned features represent fully conventional technology to one skilled in the art, wherefore they will not be described more closely herein.

For overfill prevention, the anaesthetic liquid container is provided with an intermediate container 5 which is arranged during the filling to provide a common conduit for the anaesthetic liquid and the gas removed from the anaesthetic liquid container 1. In the embodiment of FIGS. 6 to 9, the intermediate container is positioned between the filling port and the inner space of the anaesthetic liquid container. The intermediate container 5 is adapted to combine the outlet level for the liquid flow, i.e. the liquid threshold NK, and the outlet level of the gas flow, i.e. the gas threshold KK, in the filling port 4 and the anaesthetic liquid container 1 in such a way that the anaesthetic liquid is allowed to flow to the anaesthetic liquid container 1 only when the liquid flow outlet level NK is below the gas flow outlet level KK. In FIGS. 6 and 7, the subindexes 1 to 3 with the outlet levels for the liquid flow NK and for the gas flow KK refer to the similarly indexed protection directions SS, i.e. the directions of the inclinations to be protected.

Overfill prevention is thus based on the intermediate container 5, which in the embodiment of FIGS. 6 to 9 is positioned between the filling port 4 and the liquid container 1. The intermediate container 5 contains a common flow conduit for the liquid and gas flow. Thus the liquid flow outlet level NK and the gas flow outlet level KK are combined in a certain way, i.e. the liquid is allowed to flow from the bottle 2 to the liquid container 1 of the vaporizer only when the liquid flow outlet level NK is below the gas flow outlet level KK. Otherwise the intermediate container 5 is filled with liquid until the liquid surface reaches the gas flow outlet level KK, whereby the flow of replacement gas to the bottle 2 is cut off and the filling stops. The intermediate container 5 is mounted in the vaporizer in such a manner that the liquid flow outlet level, i.e. the liquid threshold NK, is below the gas flow outlet level, i.e. the gas threshold KK, in the allowable filling position, and rises above it if the vaporizer is turned to a position in which filling is not allowable.

In the example shown in the figures, the intermediate container 5 is made from a substantially U-shaped tube which is provided as an extension of the filling tube and which is preferably horizontal in relation to the normal operative position of the anaesthetic liquid container. The volume of the U-shaped tube serves as the intermediate container 5. The shape of the tube can be clearly seen from FIG. 1, in which the circled portion is also shown as a schematic perspective view. The liquid flow outlet level, i.e. the liquid threshold NK, is the highest point of the bottom of the flow conduit formed by the intermediate container 5. The gas flow outlet level, i.e. the gas threshold KK, in turn, is the lowest point of the top of the above-mentioned flow conduit. In the U-shaped tube according to the example shown in the figure, the liquid threshold NK is formed at the opening of the tube facing the vaporizer, whereas the gas threshold is formed in the upper part of the tube, at the locations indicated in the figures. When the vaporizer is tilted in such a way that the filling device rises above the liquid container 1, the liquid threshold NK rises above the gas threshold KK, and the filling stops. When the liquid flows from the supply container 2 towards the vaporizer, a liquid seal will be formed in the bend of the U-shaped tube forming the intermediate container 5. This liquid seal will prevent replacement gas from flowing to the supply container 2, whereby filling is prevented when the vaporizer is tilted. Such a situation is shown as a schematic view in FIGS. 8 and 9. The level of the liquid surface in which the filling stops is indicated in the figures by a broken line L. In addition, FIGS. 6 and 7 show the closing angle α whose significance is illustrated in principle in FIGS. 10 and 11.

In FIG. 10, the term l represents the length of the straight portion of the tube. In the bend of the tube, length may herein also refer to the length of its projection. The term d represents the diameter of the tube.

It can be seen from FIG. 10, that l=dcotα. For example, if d=7 mm and α=10°, then l=40 mm. In reality, the closing angle will be smaller because of the surface tension and viscosity of the liquid. If filling is to be prevented even in the inverted position, the flow conduit must comprise a portion whose projection in the vertical direction is greater than the diameter of the tube and which in the normal filling position extends downwards.

FIG. 11 illustrates the correlation between the diameter of the tube and the radius of curvature $r_m$ of the tube bend. It appears from FIG. 11 that the correlation between the tube diameter $r_p$ and the radius of curvature $r_m$ of the tube bend is determined by the formula $\sin \alpha = r_p/r_m$.

According to a preferred embodiment of the invention, an intermediate container 5 formed according to the principle described above can be used for emptying the container; in other words, the intermediate container 5 provided for overfill prevention is used during emptying as an emptying device. This is made possible by mounting the intermediate container in the anaesthetic liquid container in a certain manner in relation to the wall of the container that is the lowest in the emptying position, as stated above. It should also be noted that when the intermediate container 5 is formed by one tube, as shown in FIGS. 1 to 9, the arrangement must be provided with a flow passage for gas to allow the gas to flow during emptying from the transport or supply container to the anaesthetic liquid container. The flow passage can be provided by means of a separate gas conduit.

It should be noted that the intermediate container can be formed in many different ways. In its simplest, the tubular portion forming the intermediate container can be, for example, a curved tube as shown in the figure which should however be carefully positioned. The curved tubular portion, in turn, may form a bend of e.g. 90°, 180°, 270°, 360° or even greater. The curved shape can be provided in different ways, even by means of a tube that turns stepwise. The term 'curved' should be understood as a principle, the implementation of which may vary. The tubular portion can be bent so as to form a spiral. If the bending angle is 270° or greater, a liquid seal is formed during filling irrespective of the inclination angle and the position of the intermediate container. With smaller bending angles, a liquid seal is not formed in all inclination directions with the same inclination angles, but the intermediate container must then be placed in the correct position in the container to obtain a good result. The above-mentioned requirements set by the emptying process should also be taken into account.

FIGS. 12 and 13 are schematic views of an additional embodiment of the invention. FIGS. 14 to 17 show different versions of the embodiment of FIGS. 12 and 13.

The intermediate containers in the embodiments described above are made from one tube. However, this is not the only possibility. In the embodiment of FIGS. 12 and 13, the intermediate container 45 is formed from two tubes which are substantially horizontal in relation to the normal operative position of the anaesthetic liquid container and which are mounted on the same plane, parallel to one another. The cross-section shape of the tubes can be selected fully freely: it may be circular, square, etc. The embodiment of FIGS. 12 and 13 has the advantage that the maximum surface level can be accurately controlled, and the container is filled close to the maximum level at an even rate. In FIG. 13, letter A indicates the area in which filling takes place at a constant rate, and letter B the area in which filling takes place at a rate which decelerates according to the degree of fullness. It should be noted that a small inclination angle $\alpha$ is achieved with this solution. There may also be more than two parallel tubes. A construction with a plurality of tubes is preferably implemented by means of a portion forming a common inlet space 20, as shown in FIG. 12.

FIGS. 14 and 15 show different versions of the embodiment of FIGS. 12 and 13. In the solutions of FIGS. 14 and 15, the tubes that form the intermediate container 55, 65 are on different planes. In these solutions, too, the cross-section shapes of the tubes can be fully freely selected. The embodiments of FIGS. 14 and 15 operate in the same way as the embodiment of FIGS. 12 and 13. The difference is that the area B of decelerating filling is larger than in the embodiment of FIGS. 12 and 13. When the liquid surface rises to the level of the lowest tube, the liquid flow starts to slow down; when the liquid surface reaches the upper surface of the inner opening of the uppermost tube, the liquid flow stops.

FIG. 16 shows an embodiment of the solutions of FIGS. 12–13 and 14–15. In this embodiment, the intermediate container 75 is made from one tube in such a way that the area of the tube is equal to the combined area of the tubes in the solution of FIG. 14, for example. A greater inclination angle is achieved with the solution of FIG. 16 than, for instance, with the solution of FIG. 14.

FIG. 17 illustrates an embodiment in which the tubes forming the intermediate container 85 are mounted on different planes on top of one another. In this solution, the filling rate decelerates as the degree of fullness grows, i.e. when one tube is blocked, the filling rate decelerates accordingly. In this solution, too, the cross-section shapes of the tubes can be selected freely. In the examples of the figures, the tubes are mounted in succession, parallelly and/or on top of one another. The tubes can be mounted on the same plane or on different planes, or both on the same and on different planes.

In all the intermediate containers described above, the free end of the intermediate container is positioned close to the wall of the anaesthetic liquid container which is the lowest in the emptying position of the container. A particularly good result is obtained when the free end of the intermediate container is positioned in the above-mentioned liquid collection sump 6. The liquid collection sump 6 is preferably formed in the wall of the anaesthetic liquid container as part of the wall. The shape of the sump can be freely selected: it is possible to use a sump with a conical cross-section, for example. It should also be noted that when the intermediate container is formed from several tubes, it is not always necessary to have a separate gas conduit during emptying: gas can be allowed to flow during emptying from the transport or supply container to the anaesthetic liquid container through one of the tubes. It will be obvious, however, that a separate gas channel can be used even in an embodiment comprising several tubes.

FIGS. 18 to 20 show the embodiment of FIGS. 12 and 13 during filling and emptying. In the situation illustrated in FIGS. 18 and 19, the desired liquid level has just been reached. The emptying is illustrated in FIG. 20. FIG. 20 also shows an inlet space 20, which was also mentioned in connection with FIG. 12. The inlet space 20, i.e. a mixing chamber, is a space in which the gas and liquid are mixed with each other. In addition, FIG. 20 shows how the liquid flows to the transport or supply container 2 through one U-shaped tube while the gas flows in the opposite direction, i.e. to the liquid container 1, through the other U-shaped tube.

The embodiments described above are in no way intended to limit the invention, but the invention may be modified fully freely within the scope of the appended claims. It will therefore be clear that the arrangement of the invention or its details need not be precisely as shown in the figures, but other solutions are also possible. According to the figures, the intermediate container is made from a tube with a circular cross-section. As has already been stated in connection with some examples, it is not necessary to use a tube with a circular cross-section, but the intermediate container may also be formed from a tube whose cross-section is square, oval, triangular, etc.

I claim:

1. An arrangement in connection with an anaesthetic liquid container, said arrangement comprising means for conducting anaesthetic liquid during emptying of the anaesthetic liquid container from the anaesthetic liquid container to a transport or supply container connected to a filling port of the anaesthetic liquid container, and vice versa during the filling of the anaesthetic liquid container, and means for removing a volume of gas equivalent to the volume of anaesthetic liquid during emptying of the anaesthetic liquid container from the transport or supply container, and during filling correspondingly from the anaesthetic liquid container, said arrangement further comprising an intermediate container which is provided in connection with the anaesthetic liquid container and formed from a curved tubular portion and which during the filling of the anaesthetic liquid container forms a common conduit for the anaesthetic liquid and the gas removed from the liquid container, said intermediate container being further adapted during the emptying of the anaesthetic liquid container to form a conduit at least for the anaesthetic liquid discharged from the anaesthetic liquid container.

2. An arrangement according to claim 1, wherein the curved tubular portion is mounted on a substantially horizontal plane in relation to the normal operative position of the anaesthetic liquid container.

3. An arrangement according to claim 2, wherein the intermediate container is arranged to combine the liquid flow outlet level and the gas flow outlet level of the filling port and the anaesthetic liquid container in such a way that the anaesthetic liquid is allowed to flow into the anaesthetic liquid container only when the liquid flow outlet level is below the gas flow outlet level.

4. An arrangement according to claim 1, wherein the curved tubular portion is bent by at least 90°.

5. An arrangement according to claim 1, wherein the intermediate container is a substantially U-shaped tubular portion.

6. An arrangement according to claim 5, wherein the branches of the U-shaped tubular portion are mounted in a substantially horizontal position in relation to the normal operative position of the anaesthetic liquid container.

7. An arrangement according to claim 5, wherein the immediately container comprises a bottom portion and an upper portion and the highest point of the bottom portion of the intermediate container forms a liquid flow outlet level, and the lowest point of the upper portion forms a gas flow outlet level.

8. An arrangement according to claim 1, wherein the curved tubular portion is shaped as a spiral.

9. An arrangement according to claim 1, wherein the tubular portion which forms the intermediate container is made from one tube.

10. An arrangement according to claim 1, wherein the tubular portion which forms the intermediate container is made from two or more tubes.

11. An arrangement according to claim 10, wherein at least one of the tubes is arranged to form a conduit for gas removed from the transport or supply container during the emptying of the anaesthetic liquid container.

12. An arrangement according to claim 11, wherein the tubes are mounted in succession, parallelly and/or on top of one another.

13. An arrangement according to claim 12, wherein the tubes are mounted both on the same plane and on different planes.

14. An arrangement according to claim 10, wherein the tubes are mounted on the same plane.

15. An arrangement according to claim 14, wherein the tubes are mounted in succession, parallelly and/or on top of one another.

16. An arrangement according to claim 15, wherein the tubes are mounted both on the same plane and on different planes.

17. An arrangement according to claim 10, wherein the tubes are mounted on different planes.

18. An arrangement according to claim 10, wherein the tubes are mounted in succession, parallelly and/or on top of one another.

19. An arrangement according to claim 18, wherein the tubes are mounted both on the same plane and on different planes.

20. An arrangement according to claim 1, wherein the intermediate container is mounted between the filling port and the inner space of the anaesthetic liquid container in such a manner that the free end of the intermediate container is as close as possible to a wall of the anaesthetic liquid container which is the lowest when the anaesthetic liquid container is in the emptying position.

21. An arrangement according to claim 20, wherein the free end of the tubular portion forming the intermediate container, is positioned in a liquid collection sump provided inside the anaesthetic liquid container.

22. An arrangement according to claim 21, wherein the liquid collection sump is provided in connection with the wall of the anaesthetic liquid container.

23. An arrangement according to claim 22, wherein the liquid collection sump is provided as part of the wall of the anaesthetic liquid container.

24. An arrangement according to claim 1, wherein the intermediate container comprises a portion whose projection in the vertical direction is greater than the diameter of the tube.

* * * * *

UNITED STATES PATENT AND TRADEMARK OFFICE
CERTIFICATE OF CORRECTION

PATENT NO. : 5,799,710
DATED : September 1, 1998
INVENTOR(S) : Kankkunen

It is certified that error appears in the above-indentified patent and that said Letters Patent is hereby corrected as shown below:

On the title page, item
[30] Foreign Application Priority Data
    Delete "964867" and substitute therefor ---964967---

In the claims:
    Claim 7, col. 7, line 14, delete "immediately" and substitute therefor ---intermediate---

Signed and Sealed this

Ninth Day of November, 1999

Attest:

Q. TODD DICKINSON

Attesting Officer

Acting Commissioner of Patents and Trademarks